United States Patent
Fujimura et al.

[11] 3,953,467
[45] Apr. 27, 1976

[54] PYRAZOLE DERIVATIVES AND PROCESS FOR PREPARING THE SAME
[75] Inventors: Hajime Fujimu... oto; Mikio Hori, Gifu; Os... tani, Minokamo; Sa... ino, Aichi; Tadashi Kitami... Kiyoshi Kato, both of Nagoya; Mitsuaki Nagasaka, Aichi, all of Japan
[73] Assignee: Maruko Seiyaku Co., Ltd., Nagoya, Japan
[22] Filed: Apr. 17, 1974
[21] Appl. No.: 461,764

[30] Foreign Application Priority Data
Apr. 17, 1973 Japan.............................. 48-43827

[52] U.S. Cl. .............................. 260/310 R; 424/273
[51] Int. Cl.² .............. C07D 231/22; A61K 31/415
[58] Field of Search .................. 260/310 R; 424/273

[56] References Cited
OTHER PUBLICATIONS
Chemical Abstracts, Vol. 80, item 95945a, 95946b and 95947c (1974).

Primary Examiner—Donald B. Moyer
Attorney, Agent, or Firm—Sughrue, Rothwell, Mion, Zinn and Macpeak

[57] ABSTRACT
Pyrazole derivatives represented by the formula

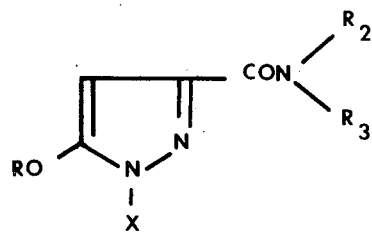

wherein R, X, $R_2$ and $R_3$ are hereinafter defined, which are useful as analgesics and anti-inflammatory agents and a process for preparing the pyrazole derivatives are disclosed.

14 Claims, No Drawings

PYRAZOLE DERIVATIVES AND PROCESS FOR PREPARING THE SAME

BACKGROUND OF THE INVENTION

FIELD OF THE INVENTION

This invention relates to novel pyrazole derivatives and, more particularly, this invention relates to novel pyrazole derivatives represented by the formula

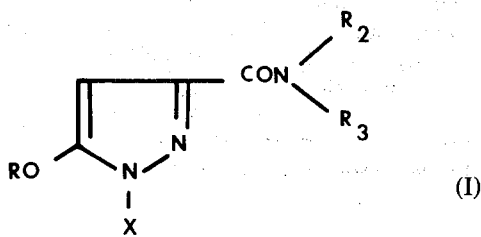

(I)

wherein R represents an alkyl group, X represents a mono- or di-substituted phenyl group wherein the substituents may be the same or different and each represents an alkyl group, an alkoxy group, a trifluoromethyl group, a nitro group, an amino group or a halogen atom; or a substituted or unsubstituted benzyl group wherein the substituent is a halogen atom, $R_2$ represents a hydrogen atom or an alkyl group and $R_3$ represents a hydrogen atom, a hydroxyalkyl group, an alkyl group or a substituted aminoalkyl group, or $R_2$ and $R_3$ may form, when taken together with the nitrogen atom to which they are attached, a 5 or 6-membered heterocyclic group which may contain one oxygen as a hetero atom, and to a process for preparing the pyrazole derivatives represented by the formula (I) above.

The pyrazole derivatives according to the present invention exhibit potent analgesic and anti-inflammatory activities and, therefore, are useful as pharmaceuticals for treating and alleviating various inflammatory conditions in animals and human.

SUMMARY OF THE INVENTION

An object of the present invention is to provide novel pyrazole derivatives which are useful as analgesics and anti-inflammatory agents.

Another object of the present invention is to provide a process for preparing such novel pyrazole derivatives.

DETAILED DESCRIPTION OF THE INVENTION

The terms "alkyl" and "alkoxy" used throughout the specification and claims of this invention means an alkyl group having 1 to 4 carbon atoms, for example, methyl, ethyl, n-propyl, iso-propyl, n-butyl, sec-butyl and tert-butyl groups and the corresponding alkoxy groups.

The term "5- or 6-membered heterocyclic group" used for the group

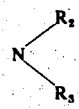

in the above formula (I) includes a pyrrolidino or pyrrolidinyl group, a piperidino or piperidinyl group, a substituted piperazino or piperazinyl group wherein the substituent is an alkyl group having 1 to 4 carbon atom such as 4-methylpiperazino, or a morpholino or morpholinyl group.

The pyrazole derivatives of the present invention represented by the formula (I) above can easily be prepared by reacting a 5-alkoxypyrazole represented by the formula

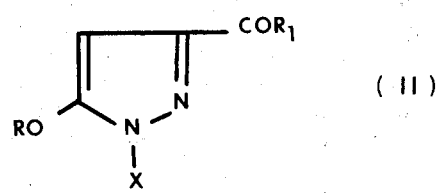

(II)

wherein R and X are as defined above, and $R_1$ represents an alkoxy group such as a methoxy or ethoxy group, a hydroxy group or a halogen atom such as a chlorine or bromine atom, with an amine represented by the formula

(III)

wherein $R_2$ and $R_3$ are as defined above. The process of this invention, i.e., an amidation of the 5-alkoxypyrazole (II), proceeds easily by reacting the 5-alkoxypyrazole with an amine corresponding to the amino group in the desired pyrazole derivative (I) in an inert organic solvent or in the presence of an excess amount of the amine which serves as both a solvent and a reactant. Generally, the reaction can be carried out in an inert organic solvent or in the presence of an excess of an amine (III) at a temperature of from about 0°C to about 80°C using at least an equimolar amount of the amine relative to a 5-alkoxypyrazole for a period of from about 20 minutes to about 16 hours.

The reaction conditions employed in the process of this invention somewhat vary depending upon the type of the starting material, in particular, the type of the substituent $R_1$ in the 5-alkoxypyrazole (II) reaction.

When $R_1$ represents an alkoxy group, i.e., the substituent at 3-position of the starting material (II) represents an alkyl ester —$COOR_1$, the amidation can conveniently be carried out in an organic solvent such as alkanols having 1 to 4 carbon atoms, for example, methanol, ethanol and the like or benzene using about 1 to about 5 moles, preferably 2 to 5 moles of an amine per 1 mole of the 5-alkoxypyrazole while heat-refluxing the reaction mixture, generally at a temperature of from about 60 to about 80°C, for a period of from about 1 to about 5 hours. A well-known condensing agent such as aluminum isopropoxide or sodium amide can be used in the amidation reaction to ensure a smooth reaction but the use of such a condensing agent is not essential. Alternatively, when the amine of the formula (III) has a low boiling point, e.g., in the range of below about 50°C under atmospheric pressure, the reaction is advantageously carried out in a sealed reaction vessel under a pressurized condition, for example, in an autoclave under an autogenous pressure.

When $R_1$ represents a —OH group, i.e., the substituent at 3-position of the starting material (II) represents a carboxy group —COOH, the amidation can advantageously be carried out in an inert organic solvent such as methylene chloride, chloroform and the like in the presence of a dehydrating agent, for example, N,N'-dicyclohexylcarbodiimide at a temperature of from ice-cooling temperature (about 10°C) to room temperature (about 25°C) for a period of from about 3 to about 16 hours, preferably 8 to 16 hours. In this reaction, the amine can advantageously be used from 1 to 2 moles per 1 mole of the 5-alkoxypyrazole (II).

When $R_1$ represents a halogen atom, i.e., the substituent at 3-position of the starting material (II) represents an acid halide group, the amidation can easily be carried out by reacting an acid halide (II) with an amine (III) in an inert organic solvent such as ethyl ether, chloroform, benzene, pyridine, triethylamine and the like at a temperature of from ice-cooling temperature to room temperature for a period of from about 20 minutes to about 2 hours, preferably from 30 minutes to 1 hour. In this reaction, the amine reactant can advantageously be used in an excess amount, for example, from 2 to 5 molar excess so as to serve as an reactant as well as a reaction solvent.

The present invention also includes the pharmaceutically acceptable acid addition salts of the pyrazole derivatives of the formula (I). These acid addition salts can be prepared from the free base compound (I) by the conventional procedure, for example, by introducing hydrogen chloride gas into a solution of the free base compound in an organic solvent such as methanol to form the corresponding hydrochloride salt of the pyrazole derivatives. Typical examples of the pharmaceutically acceptable acid addition salts of the pyrazole derivatives (I) are hydrochloride, sulfate, phosphate, oxalate, fumarate, maleate, tartarate and the like.

As described previously, the pyrazole derivatives represented by the above formula (I) exhibit potent analgesic and anti-inflammatory activities. For example, 1-(p-tolyl)-3-N,N-dimethylcarbamoyl-5-methoxypyrazole (Compound A), 1-(m-trifluoromethylphenyl)-3-N,N-dimethylcarbamoyl-5-n-butoxypyrazole (Compound B), 1-(m-chlorophenyl)-3-N,N-dimethylcarbamoyl-5-methoxypyrazole (Compound C), 1-(m-chlorophenyl)-3-carbamoyl-5-methoxypyrazole (Compound D) and 1-(p-chlorobenzyl)-3-N-methylcarbamoyl-5-methoxypyrazole (E) exhibit an excellent analgesic activity as determined by the acetic acid stretching method and the pressure-stimulation method.

Acetic Acid Stretching Method

Each of the test compounds (Compounds A to E) was administered orally to ddN male mice weighing 17 to 20 g (5 to 7 mice per group) and 30 minutes after administration, a 0.7% aqueous solution of acetic acid was administered intraperitoneally to the mice in a dose of 0.1 ml per 10 g of the body weight. The number of stretching of the mice for a period of 5 minutes was then counted 15 and 30 minutes after the administration of the aqueous acetic acid and compared with the number of stretching in the control group which received only the aqueous acetic acid to determine the percent inhibitory of the test compounds. In this experiment, Compounds A to E were found to have a stretching inhibitory activity (analgesic activity) of 2.0, 4.0, 3.4, 2.2 and 1.6 times, respectively, higher than that of aminopyrine.

Pressure-Stimulation Method

Each of the test compounds (Compounds A to E) was administered orally to ddN male mice weighing 18 to 20 g (8 to 10 mice per group), and the pressure was applied to the tail using a pressure-stimulation apparatus (Takagi et al apparatus). The reaction of the mice, i.e., turning of the head toward the stimulated portion and biting behavior, was observed as a criterion and the pain threshold was determined. In this experiment, Compounds A to E were found to have an analgesic activity of 1.8, 1.6, 2.5, 2.0 and 1.8 times, respectively, higher than that of aminopyrine.

The compounds of this invention also possess an excellent anti-inflammatory activity as determined by the well-established carrageenin-induced edema inhibitory activity.

Carrageenin-Induced Edema Inhibitory Activity

Each of the test compounds (Compounds A to E) was administered orally to Wister male rats weighing about 150 g (7 to 8 rats per group) and 30 minutes after the administration of the test compound, 0.1 ml of a 1% aqueous solution of carrageenin was administered subcutaneously to a hind paw of the rats. Thereafter, the volume of the paw was measured at an interval of 1 hour to determine the swelling ratio of the paw relative to the volume of the same paw before administration of the aqueous carrageenin. The edema inhibitory activity was calculated by comparing the swelling ratio in the control group which received only the test compounds. In this experiment, Compounds A to E were found to have an edema inhibitory activity of 1.8, 2.0, 3.5, 2.2 and 1.9 times, respectively, higher than that of aminopyrine.

The acute toxicity of the test compounds was also determined in rats by oral administration in the standard method and found to be 1620 mg/kg, 760 mg/kg, 950 mg/kg, 930 mg/kg and 540 mg/kg, respectively in terms of a 50% lethal dose ($LD_{50}$).

The present invention is further illustrated by the following Examples, but they are not to be construed as limiting the scope of this invention.

EXAMPLE 1

1-(m-Trifluoromethylphenyl)-3-N,N-dimethylcarbamoyl-5-n-butoxypyrazole 34.7 g of 1-(m-trifluoromethylphenyl)-5-n-butoxypyrazol-3-yl carbonyl chloride was dissolved in 150 ml of ethyl ether, and to the resulting solution was added dropwise 50 ml of a solution containing 11 g of dimethylamine in ethyl ether while cooling the mixture to a temperature of 10°C with stirring. After allowing to stand for 1 hour, the reaction mixture was washed successively with 5% hydrochloric acid, 5% aqueous sodium carbonate and water. The ethereal layer was separated and dried over anhydrous sodium sulfate. The solvent (ethyl ether) was then removed by distillation and the resulting residue was recrystallized from n-pentane to give 29.8 g (83.9% yield) of 1-(m-trifluoromethylphenyl)-3-N,N-dimethylcarbamoyl-5-n-butoxypyrazole as colorless prisms having a melting point of 66° to 68°C.
Analysis Calcd. for $C_{17}H_{20}O_2N_3F_3$ (Molecular Weight: 355.4): C, 57.46; H, 5.67; N, 11.82. Found: C, 57.62; H, 5.75; N, 11.84.

EXAMPLE 2

1-(p-Tolyl)-3-N,N-dimethylcarbamoyl-5-methoxypyrazole 23.2 g of 1-(p-tolyl)-3-carboxy-5-methoxypyrazole was dissolved in 100 ml of chloroform, and to the resulting solution was added a solution containing 4 g of dimethylamine in 20 ml of chloroform while cooling the mixture to a temperature of 5° to 10°C with stirring. 50 ml of a solution of 10 g of N,N-dicyclohexylcarbodiimide in chloroform was then added dropwise to the resulting mixture and, after completion of the addition, the mixture was allowed to cool to room temperature followed by stirring for 7 hours. The reaction mixture was then made acidic with acetic acid and the precipitated crystals were then removed by filtration. The solvent was removed from the filtrate by distillation and the resulting residue was washed successively with 5% aqueous sodium hydroxide and water. Recrystallization from ethyl ether-petroleum ether gave 12 g (46.3% yield) of 1-(p-tolyl)-3-N,N-dimethylcarbamoyl-5-methoxypyrazole is colorless prisms having a melting point of 120° – 121°C.

Analysis

Calcd. for $C_{14}H_{17}O_2N_3$ (Molecular Weight: 259.3) C, 64.85; H, 6.61; N, 16.20. Found: C, 65.06; H, 6.54; N, 16.07.

The combined washings obtained above, i.e., the 5% aqueous sodium hydroxide and water, was made acidic with hydrochloric acid and the precipitated crystals were separated by filtration to recover 10.3 g (44.4% yield) of the unreacted starting material, 1-(p-tolyl)-3-carboxy-5-methoxypyrazole.

EXAMPLE 3

1-(p-Chlorobenzyl)-3-carbamoyl-5-n-butoxypyrazole

A mixture consisting of 6.7 g of 1-(p-chlorobenzyl)-3-ethoxycarbonyl-5-n-butoxypyrazole, 30 ml of a 28% aqueous ammonia solution and 30 ml of methanol was placed in an autoclave and heated at a temperature of 60°C for 2 hours. After completion of the reaction, the solvent was removed by distillation and the residue was recrystallized from methanol-petroleum ether to give 5.3 g (86.2% yield) of 1-(p-chlorobenzyl)-3-carbamoyl-5-n-butoxypyrazole as colorless needles having a melting point of 137° – 138°C.

Analysis

Calcd. for $C_{15}H_{18}O_2N_3Cl$ (Molecular Weight: 307.8): C, 58.54; H, 5.89; N, 13.65. Found: C, 58.66; H, 5.86; N, 13.62.

EXAMPLE 4

1-(p-Chlorobenzyl)-3-(4'-methylpiperazinyl)-carbonyl-5-methoxypyrazole hydrochloride 5.7 g of 1-(p-chlorobenzyl)-5-methoxypyrazol-3-yl carbonyl chloride was dissolved in 60 ml of benzene, and to the resulting solution was added dropwise 3 g of N-methylpiperazine with stirring. After allowing the reaction mixture to stand for 20 minutes, the mixture was washed well successively with 10% aqueous sodium hydroxide and water. The benzene layer was then separated and dried, and the benzene was then removed by distillation. The resulting residue was dissolved in methanol and hydrogen chloride gas was introduced into the methanolic solution. The methanol was then removed by distillation and the resulting crystals were recrystallized from methanol-ethyl ether to give 5.4 g (70.1% yield) of 1-(p-chlorobenzyl)-3-(4'-methylpiperazinyl)-carbonyl-5methoxypyrazole hydrochloride as a colorless crystalline powder having a melting point of 223° to 225°C (with decomposition).

Analysis

Calcd. for $C_{17}H_{21}O_2N_4Cl\cdot HCl$ (Molecular Weight: 385.3): C, 53.00; H, 5.76; N, 14.54. Found: C, 52.94; H, 5.83; N, 14.41.

EXAMPLE 5

1-(p-Chlorophenyl)-3-N,N-dimethylcarbamoyl-5-n-butoxypyrazole

A mixture consisting of 16.1 g of 1-(p-chlorophenyl)-3-ethoxycarbonyl-5-n-butoxypyrazole, 4 g of dimethylamine and 200 ml of ethanol was placed in an autoclave and heated at a temperature of from 70° to 80°C for 4 hours with stirring. After completion of the reaction, the solvent was removed by distillation, and the residue was washed successively with 5% hydrochloric acid and water. Recrystallization from ethyl ether-petroleum ether gave 11.8 g (73.3% yield) of 1-(p-chlorophenyl)-3-N,N-dimethylcarbamoyl-5-n-butoxypyrazole as colorless needles having a melting point of 94 to 95°C.

Analysis

Calcd. for $C_{16}H_{20}O_2N_3Cl$ (Molecular Weight: 321.8): C, 59.72; H, 6.26; N, 13.06. Found: C, 59.85; H, 6.31; N, 12.98.

EXAMPLE 6

1-(p-Tolyl)-3-N,N-dimethylcarbamoyl-5-n-butoxypyrazole 29.3 g of 1-(p-tolyl)-5-n-butoxypyrazol-3-yl carbonyl chloride was dissolved in 150 ml of benzene, and to the resulting solution was added dropwise a solution of 11 g of dimethylamine in 50 ml of benzene while maintaining the mixture at a temperature of from 10 to 15°C with stirring. The reaction mixture was then worked up in the same manner as described in Example 1 and the product thus obtained was recrystallized from ethyl ether-petroleum ether to give 24.1 g (80.0% yield) of 1-(p-tolyl)-3-N,N-dimethylcarbamoyl-5-n-butoxypyrazole as colorless plates having a melting point of 99 – 100°C.

Analysis

Calcd. for $C_{17}H_{23}O_2N_3$ (Molecular Weight: 301.4): C, 67.75; H, 7.69; N, 13.94. Found: C, 67.78; H, 7.78; N, 13.81.

EXAMPLE 7

1-(p-Chlorophenyl)-3-N,N-dimethylcarbamoyl-5-methoxypyrazole 25.3 g of 1-(p-chlorophenyl)-3-carboxy-5-methoxypyrazole was dissolved in 100 ml of methylene chloride, and to the resulting solution was added dropwise a solution of 4 g of dimethylamine in 20 ml of methylene chloride while maintaining the mixture at a temperature of from 5 to 10°C with stirring. A solution of 10 g of N,N-8-dicyclohexylcarbodiimide in 50 ml of methylene chloride was then added dropwise to the mixture. The reaction mixture was then worked up in the same manner as described in Example 2 and the product thus obtained was recrystallized from ethyl ether-petroleum ether to give 12.7 g (45.4% yield) of 1-(p-chlorophenyl)-3-N,N-dimethylcarbamoyl-5-methoxypyrazole as colorless prisms having a melting point of 116° – 118°C.

Analysis

Calcd. for $C_{13}H_{14}O_2N_3Cl$ (Molecular Weight: 279.7): C, 55.82; H, 5.04; N, 15.02. Found: C, 55.75; H, 5.06; N, 15.02.

In the same manner as described in the proceeding Examples, the following compounds were also prepared from a 5-alkoxypyrazole (II) and an amine (III).

| Example No. | Compound | Crystal form | Recrystallization solvent | Melting point | Empirical formula (M. W.) | Analysis (%) Calcd. (Found) C | H | N |
|---|---|---|---|---|---|---|---|---|
| 8 | 1-(p-tolyl-3-N,N-dimethyl-carbamoyl-5-isopropoxy-pyrazole | Colorless Prisms | Ethyl ether-petroleum ether | 90–91 | $C_{16}H_{21}O_2N_3$ (287.4) | 66.88 (66.78 | 7.34 7.45 | 14.62 14.68) |
| 9 | 1-(p-chlorophenyl)-3-N,N-dimethylcarbamoyl-5-ethoxypyrazole | Colorless Needles | Ethyl ether-petroleum ether | 107–108 | $C_{14}H_{16}O_2N_3Cl$ (293.8) | 57.24 (57.20 | 5.49 5.50 | 14.30 14.14) |
| 10 | 1-(p-chlorophenyl)-3-N,N-dimethylcarbamoyl-5-n-propoxypyrazole | Colorless Prisms | Ethyl ether-petroleum ether | 83–84 | $C_{15}H_{18}O_2N_3Cl$ (307.8) | 58.54 (58.71 | 5.89 5.95 | 13.65 13.66) |
| 11 | 1-(m-chlorophenyl)-3-N,N-dimethylcarbamoyl-5-methoxypyrazole | Colorless Prisms | Ethyl ether | 98–99 | $C_{13}H_{14}O_2N_3Cl$ (279.7) | 55.82 (56.01 | 5.04 5.01 | 15.02 14.94) |
| 12 | 1-(m-trifluoromethylphenyl)-3-N,N-dimethylcarbamoyl-5-n-propoxypyrazole | Colorless Prisms | Petroleum benzine | 83–84 | $C_{16}H_{18}O_2N_3F_3$ (341.3) | 56.30 (56.17 | 5.32 5.33 | 12.31 12.33) |
| 13 | 1-(m-trifluoromethylphenyl)-3-N,N-dimethylcarbamoyl-5-ethoxypyrazole | Colorless Needles | Petroleum benzine | 83–84 | $C_{15}H_{16}O_2N_3F_3$ (327.3) | 55.05 (55.21 | 4.93 4.98 | 12.84 12.83) |
| 14 | 1-(m-trifluoromethylphenyl)-3-N,N-dimethylcarbamoyl-5-methoxypyrazole | Colorless Needles | Benzene-petroleum ether | 116–117 | $C_{14}H_{14}O_2N_3F_3$ (313.3) | 53.68 (53.75 | 4.50 4.41 | 13.41 13.20) |
| 15 | 1-(p-tolyl)-3-morpholino-carbonyl-5-methoxypyrazole | Colorless Oil | — | b.p. 130–131/2 mmHg | $C_{16}H_{19}O_3N_3$ (301.3) | 63.77 (63.93 | 6.36 6.45 | 13.94 13.76) |
| 16 | 1-(p-chlorophenyl)-3-(4'-methylpiperazinyl)-carbonyl-5-methoxypyrazole | Colorless Needles | Ethanol-Petroleum ether-Ethyl ether | 116–117 | $C_{16}H_{19}O_2N_4Cl$ (334.8) | 57.40 (57.34 | 5.72 5.79 | 16.73 16.52) |
| 17 | 1-(m-chlorophenyl)-3-N,N-diisopropylcarbamoyl-5-methoxypyrazole | Colorless Prisms | Ethyl ether-Petroleum ether | 102–103 | $C_{17}H_{22}O_2N_3Cl$ (335.8) | 60.80 (60.86 | 6.60 6.53 | 12.51 12.37) |
| 18 | 1-(m-chlorophenyl)-3-morpholinocarbonyl-5-methoxypyrazole | Colorless Needles | Ethyl ether-Petroleum ether | 73–74 | $C_{15}H_{16}O_3N_3Cl$ (321.8) | 55.99 (56.06 | 5.01 4.94 | 13.06 13.02) |
| 19 | 1-(m-chlorophenyl)-3-(4'-methylpiperazinyl)-carbonyl-5-methoxypyrazole | Colorless Crystalline Powder | Ethyl ether-Petroleum ether | 76–77 | $C_{16}H_{19}O_2N_4Cl$ (334.8) | 57.40 (57.36 | 5.72 5.64 | 16.73 16.64) |
| 20 | 1-(p-chlorophenyl)-3-N,N-diisopropylcarbamoyl-5-methoxypyrazole | Colorless Plates | Methanol-Petroleum ether | 126–127 | $C_{17}H_{22}O_2N_3Cl$ (335.8) | 60.80 (60.68 | 6.60 6.61 | 12.51 12.59) |
| 21 | 1-(p-tolyl)-3-N,N-diisopropylcarbamoyl-5-methoxypyrazole | Colorless Plates | Ethanol-Petroleum ether | 95–96 | $C_{17}H_{25}O_2N_3$ (303.4) | 67.30 (67.47 | 8.31 8.27 | 13.85 13.72) |
| 22 | 1-(p-chlorophenyl)-3-morpholinocarbonyl-5-methoxypyrazole | Colorless Needles | Ethanol-Petroleum ether | 109–110 | $C_{14}H_{16}O_3N_3Cl$ (309.8) | 54.29 (54.16 | 5.21 5.21 | 13.57 13.55) |
| 23 | 1-(p-chlorophenyl)-3-(pyrrolidin-1-yl)-carbonyl-5-methoxypyrazole | Colorless Needles | Ethanol-Petroleum ether | 156–158 | $C_{15}H_{16}O_2N_3Cl$ (305.8) | 58.92 (58.98 | 5.27 5.34 | 13.74 13.58) |
| 24 | 1-(p-chlorophenyl)-3-N-methylcarbamoyl-5-methoxypyrazole | Colorless Crystalline Powder | Ethanol-Petroleum ether | 121–122 | $C_{12}H_{12}O_2N_3Cl$ (265.7) | 54.25 (54.25 | 4.55 4.44 | 15.81 15.94) |
| 25 | 1-(p-chlorophenyl)-3-N-n-butylcarbamoyl-5-methoxypyrazole | Colorless Prisms | Ethanol-Petroleum ether | 53–54 | $C_{15}H_{18}O_2N_3Cl$ (307.8) | 58.54 (58.69 | 5.89 5.86 | 13.65 13.51) |
| 26 | 1-(m-chlorophenyl)-3-N-methylcarbamoyl-5-methoxypyrazole | Colorless Crystalline Powder | Ethyl ether-Petroleum ether | 136–137 | $C_{12}H_{12}O_2N_3Cl$ (265.7) | 54.25 (54.42 | 4.55 4.61 | 15.81 15.72) |
| 27 | 1-(m-chlorophenyl)-3-N-sec-butylcarbamoyl-5-methoxypyrazole | Colorless Needles | Ethyl ether-Petroleum ether | 96–97 | $C_{15}H_{18}O_2N_3Cl$ (307.8) | 58.54 (58.67 | 5.89 5.93 | 13.65 13.50) |
| 28 | 1-(m-chlorophenyl)-3-(pyrrolidin-1-yl)-carbonyl-5-methoxypyrazole | Colorless Prisms | Ethyl ether-Petroleum ether | 111–112 | $C_{15}H_{16}O_2N_3Cl$ (305.8) | 58.92 (59.13 | 5.27 5.30 | 13.74 13.71) |
| 29 | 1-(o-chlorophenyl)-3-N,N-dimethylcarbamoyl-5-methoxypyrazole | Colorless Plates | Methanol-Petroleum ether | 142–144 | $C_{13}H_{14}O_2N_3Cl$ (279.7) | 55.82 (55.96 | 5.04 5.08 | 15.02 15.01) |
| 30 | 1-(m-chlorophenyl)-3-N-methylcarbamoyl-5-n-butoxypyrazole | Colorless Needles | Ethyl ether-Petroleum ether | 77–78 | $C_{15}H_{18}O_2N_3Cl$ (307.8) | 58.54 (58.51 | 5.89 5.93 | 13.65 13.52) |
| 31 | 1-(m-chlorophenyl)-3-N,N-dimethylcarbamoyl-5-n-butoxypyrazole | Colorless Plates | Ethyl ether-Petroleum ether | 63–64 | $C_{16}H_{20}O_2N_3Cl$ (321.8) | 59.72 (59.86 | 6.26 6.24 | 13.06 12.89) |
| 32 | 1-(m-chlorophenyl)-3-(pyrrolidin-1-yl)-carbonyl-5-n-butoxypyrazole | Colorless Needles | Ethyl ether-Petroleum ether | 81–82 | $C_{18}H_{22}O_2N_3Cl$ (347.8) | 62.15 (62.32 | 6.38 6.40 | 12.08 12.12) |
| 33 | 1-(m-chlorophenyl)-3-carbamoyl-5-methoxypyrazole | Colorless Needles | Ethyl acetate | 150–152 | $C_{11}H_{10}O_2N_3Cl$ (251.7) | 52.50 (52.57 | 4.01 4.03 | 16.70 16.61) |
| 34 | 1-(m-chlorophenyl)-3-N-ethylcarbamoyl-5- | Colorless Needles | Ethyl ether-Petroleum | 85–86 | $C_{13}H_{14}O_2N_3Cl$ (279.7) | 51.53 (51.65 | 5.04 5.00 | 15.02 14.88) |

-continued

| Example No. | Compound | Crystal form | Recrystallization solvent | Melting point | Empirical formula (M.W.) | Analysis (%) Calcd. (Found) C | H | N |
|---|---|---|---|---|---|---|---|---|
| | methoxypyrazole | | benzine | | | | | |
| 35 | 1-(m-chlorophenyl)-3-N-n-butylcarbamoyl-5-methoxypyrazole | Colorless Oil | — | b.p. 215/ 1 mmHg | $C_{15}H_{18}O_2N_3Cl$ (307.8) | 58.54 (58.71 | 5.89 5.96 | 13.65 13.52) |
| 36 | 1-(m-chlorophenyl)-3-N-(2'-hydroxyethyl)-carbamoyl-5-methoxypyrazole | Colorless Needles | Ethanol-Petroleum ether | 143–145 | $C_{13}H_{14}O_3N_3Cl$ (295.7) | 52.80 (52.93 | 4.77 4.81 | 14.21 14.20) |
| 37 | 1-(m-chlorophenyl)-3-N,N-diethylcarbamoyl-5-methoxypyrazole | Colorless Needles | Ethyl ether-Petroleum ether | 76–77 | $C_{15}H_{18}O_2N_3Cl$ (307.8) | 58.54 (58.67 | 5.89 5.87 | 13.65 13.59) |
| 38 | 1-(m-chlorophenyl)-3-N-methyl-N-(2'-hydroxyethyl)-carbamoyl-5-methoxypyrazole | Colorless Oil | — | | $C_{14}H_{16}O_3N_3Cl$ (309.8) | 54.29 (54.17 | 5.21 5.30 | 13.57 13.39) |
| 39 | 1-(m-chlorophenyl)-3-(piperidin-1-yl)-carbonyl-5-methoxypyrazole | Colorless Oil | — | b.p. 215/ 5 mmHg | $C_{16}H_{18}O_2N_3Cl$ (319.8) | 60.09 (60.26 | 5.67 5.59 | 13.14 13.06) |
| 40 | 1-(m-chlorophenyl)-3-N-(N',N'-diethylaminoethyl)-carbamoyl-5-n-butoxypyrazole oxalate | Colorless Crystalline Powder | Methanol-Petroleum ether | 130–132 | $C_{20}H_{29}O_2N_4Cl$. $C_2H_2O_4$ (483.0) | 54.71 (54.89 | 6.47 6.62 | 11.60 11.38) |
| 41 | 1-(m-chlorophenyl)-3-N-(N',N'-diethylaminoethyl)-carbamoyl-5-methoxypyrazole oxalate | Colorless Crystalline Powder | Methanol-Petroleum ether | 141–143 | $C_{17}H_{23}O_2N_4Cl$. $C_2O_2H_2$ (440.9) | 51.76 (51.62 | 5.72 5.76 | 12.71 12.54) |
| 42 | 1-(p-chlorophenyl)-3-N-(N',N'-diethylaminoethyl)-carbamoyl-5-methoxypyrazole oxalate dihydrate | Colorless Crystalline Powder | Methanol-Ethyl acetate | 170–171 (decomposition) | $C_{17}H_{23}O_2N_4Cl$. $2H_2O.C_2H_2O_4$ (476.9) | 47.85 (48.06 | 6.13 6.15 | 11.75 11.64) |
| 43 | 1-(m-nitrophenyl)-3-N,N-dimethylcarbamoyl-5-methoxypyrazole | Colorless Needles | Hydrated acetone | 147–148 | $C_{13}H_{14}O_4N_4$ (290.3) | 53.79 (53.92 | 4.86 4.73 | 19.30 19.31) |
| 44 | 1-(m-aminophenyl)-3-N,N-dimethylcarbamoyl-5-methoxypyrazole | Colorless Needles | Ethyl acetate | 118–119 | $C_{13}H_{16}O_2N_3$ (260.3) | 59.99 (60.18 | 6.20 6.04 | 21.52 21.36) |
| 45 | 1-(p-chlorobenzyl)-3-N-methylcarbamoyl-5-methoxypyrazole | Colorless Needles | Ethyl ether-Petroleum ether | 93–95 | $C_{13}H_{14}O_2N_3Cl$ (279.7) | 55.82 (55.95 | 5.04 5.13 | 15.02 15.01) |
| 46 | 1-(p-chlorobenzyl)-3-N-sec-butylcarbamoyl-5-methoxypyrazole | Colorless Granules | Ethyl ether-Petroleum ether | 63–64 | $C_{16}H_{20}O_2N_3Cl$ (321.8) | 59.72 (59.93 | 6.26 6.35 | 13.06 12.92) |
| 47 | 1-(3,4-dichlorophenyl)-3-N,N-dimethylcarbamoyl-5-methoxypyrazole | Colorless Needles | Hydrated Methanol | 107–108 | $C_{13}H_{13}O_2N_3Cl_2$ (314.2) | 49.70 (49.78 | 4.17 4.15 | 13.37 13.24) |
| 48 | 1-(3,4-dichlorophenyl)-3-N-(N',N'-diethylaminoethyl)-carbamoyl-5-methoxypyrazole | Colorless Needles | Ethyl ether-Petroleum ether | 64–65 | $C_{17}H_{22}O_2N_4Cl_2$ (385.3) | 53.00 (52.94 | 5.76 5.70 | 14.54 14.68) |
| 49 | 1-(p-chlorobenzyl)-3-N,N-dimethylcarbamoyl-5-methoxypyrazole | Colorless Flakes | Isopropyl ether-Petroleum benzine | 70–71 | $C_{14}H_{16}O_2N_3Cl$ (293.8) | 57.24 (57.37 | 5.49 5.52 | 14.30 14.21) |
| 50 | 1-(p-chlorobenzyl)-3-morpholinocarbonyl-5-methoxypyrazole | Colorless Needles | Ligroin | 115–117 | $C_{16}H_{18}C_3N_3Cl$ (335.8) | 57.23 (57.38 | 5.40 5.32 | 12.51 12.29) |
| 51 | 1-(p-chlorobenzyl)-3-N-n-butylcarbamoyl-5-methoxypyrazole | Colorless to Pale Yellow Oil | — | b.p. 248/ 6 mmHg | $C_{16}H_{20}O_2N_3Cl$ (321.8) | 59.72 (59.93 | 6.26 6.37 | 13.06 12.88) |
| 52 | 1-(p-chlorobenzyl)-3-N,N-diisopropylcarbamoyl-5-methoxypyrazole | Colorless Prisms | Ethyl ether-Petroleum ether | 89–90 | $C_{18}H_{24}O_2N_3Cl$ (349.9) | 61.80 (61.63 | 6.91 6.92 | 12.01 11.86) |
| 53 | 1-(p-chlorobenzyl)-3-(pyrrolidin-1-yl)-carbonyl-5-methoxypyrazole | Colorless Needles | Ethyl ether-Petroleum ether | 97–99 | $C_{16}H_{18}O_2N_3Cl$ (319.8) | 60.09 (60.26 | 5.67 5.67 | 13.14 13.12) |
| 54 | 1-(p-chlorobenzyl)-3-carbamoyl-5-methoxypyrazole | Colorless Plates | Ethyl acetate | 144–146 | $C_{12}H_{12}O_2N_3Cl$ (265.7) | 54.25 (54.38 | 4.55 4.62 | 15.81 15.68) |
| 55 | 1-(p-chlorobenzyl)-3-N-(N',N'-diethylaminoethyl)-carbamoyl-5-methoxypyrazole oxalate | Colorless Crystalline Powder | Ethanol-Ethyl ether | 155–157 (decomposition) | $C_{18}H_{25}O_2N_4Cl$. $C_2H_2O_4$ (454.9) | 52.81 (52.58 | 5.98 6.12 | 12.32 12.16) |
| 56 | 1-(p-chlorobenzyl)-3-N-methylcarbamoyl-5-n-butoxypyrazole | Colorless Flakes | Methanol-Petroleum ether | 124–125 | $C_{16}H_{20}O_2N_3Cl$ (321.8) | 59.72 (59.68 | 6.26 6.30 | 13.06 13.22) |
| 57 | 1-(p-chlorobenzyl)-3-N-n-butylcarbamoyl-5-n-butoxypyrazole | Colorless Needles | Ethyl ether-Petroleum ether | 70–71 | $C_{19}H_{26}O_2N_3Cl$ (363.9) | 62.71 (62.88 | 7.20 7.28 | 11.55 11.36) |
| 58 | 1-(p-chlorobenzyl)-3-N,N-dimethylcarbamoyl-5-n-butoxypyrazole | Colorless Needles | Ethyl ether-Petroleum ether | 60–61 | $C_{17}H_{22}O_2N_3Cl$ (335.8) | 60.80 (60.87 | 6.60 6.59 | 12.51 12.37) |
| 59 | 1-(p-chlorobenzyl)-3-morpholinocarbonyl-5-n-butoxypyrazole | Colorless Needles | Ethyl ether-Petroleum ether | 85–86 | $C_{19}H_{24}O_3N_3Cl$ (377.9) | 60.39 (60.53 | 6.40 6.28 | 11.12 11.15) |
| 60 | 1-(p-chlorobenzyl)-3-N,N-diisopropylcarbamoyl-5-n-butoxypyrazole | Colorless Granules | Ethyl ether-Petroleum ether | 73–74 | $C_{21}H_{30}O_2N_3Cl$ (391.9) | 64.35 (64.38 | 7.72 7.63 | 10.72 10.59) |
| 61 | 1-(p-chlorobenzyl)-3-(pyrrolidin-1-yl)-carbonyl-5-n-butoxypyrazole | Colorless Needles | Ethyl ether-Petroleum ether | 86–87 | $C_{19}H_{24}O_2N_4Cl$ (361.9) | 63.06 (63.27 | 6.68 6.67 | 11.61 11.59) |
| 62 | 1-(p-chlorobenzyl)-3-N-(N',N'-diethylaminoethyl)-carbamoyl-5-n-butoxypyrazole | Colorless Crystalline Powder | Ethanol-Ethyl ether | 138–140 | $C_{21}H_{31}O_2N_4Cl$. $C_2H_2O_4$ (497.0) | 55.59 (55.76 | 6.69 6.73 | 11.27 11.11) |

-continued

| Example No. | Compound | Crystal form | Recrystallization solvent | Melting point | Empirical formula (M.W.) | Analysis (%) Calcd. (Found) | | |
|---|---|---|---|---|---|---|---|---|
| | | | | | | C | H | N |
| 63 | 1-(p-chlorobenzyl)-3-(4'-methylpiperazinyl)-carbonyl-5-n-butoxypyrazole | Colorless Needles | Acetone-Petroleum ether | 92–93.5 | $C_{20}H_{27}O_2N_4Cl$ (390.9) | 61.45 (61.62 | 6.96 6.85 | 14.33 14.26) |
| 64 | 1-(o-chlorobenzyl)-3-carbamoyl-5-methoxypyrazole | Colorless Needles | Hydrated ethanol | 163–164 | $C_{12}H_{12}O_2N_3Cl$ (265.7) | 54.25 (54.29 | 4.55 4.48 | 15.81 15.73) |
| 65 | 1-(o-chlorobenzyl)-3-N-methylcarbamoyl-5-methoxypyrazole | Colorless Needles | Ethanol-Petroleum ether | 131–132 | $C_{13}H_{14}O_2N_3Cl$ (279.7) | 55.82 (55.98 | 5.04 5.05 | 15.02 15.00) |
| 66 | 1-(o-chlorobenzyl)-3-N,N-dimethylcarbamoyl-5-methoxypyrazole | Colorless Needles | Ethanol-Petroleum ether | 135–136 | $C_{14}H_{16}O_2N_3Cl$ (293.8) | 57.24 (57.41 | 5.49 5.46 | 14.30 13.36) |
| 67 | 1-(o-chlorobenzyl)-3-N,N-diisopropylcarbamoyl-5-methoxypyrazole | Colorless Prisms | Ethanol-Petroleum ether | 130–131 | $C_{18}H_{24}O_2N_3Cl$ (349.9) | 61.80 (61.72 | 6.91 6.97 | 12.01 11.82) |
| 68 | 1-(o-chlorobenzyl)-3-(4'-methylpiperazinyl)-carbonyl-5-methoxypyrazole | Colorless Prisms | Ethanol-Petroleum ether | 91–92 | $C_{17}H_{21}O_2N_4Cl$ (348.8) | 58.53 (58.69 | 6.07 6.13 | 16.06 15.93) |
| 69 | 1-(m-bromophenyl)-3-carbamoyl-5-methoxypyrazole | Colorless Needles | Hydrated Methanol | 159–161 | $C_{11}H_{10}O_2N_3Br$ (296.1) | 44.62 (44.63 | 3.40 3.41 | 14.19 14.13) |
| 70 | 1-(m-bromophenyl)-3-N-methylcarbamoyl-5-methoxypyrazole | Colorless Prisms | Ethyl ether-Petroleum ether | 109–110 | $C_{12}H_{12}O_2N_3Br$ (310.2) | 46.47 (46.61 | 3.90 3.83 | 13.55 13.32) |
| 71 | 1-(m-bromophenyl)-3-N-ethylcarbamoyl-5-methoxypyrazole | Colorless Prisms | Ethyl ether-Petroleum ether | 80–81 | $C_{13}H_{14}O_2N_3Br$ (324.2) | 48.17 (48.25 | 4.35 4.23 | 12.96 12.78) |
| 72 | 1-(m-bromophenyl)-3-N,N-dimethylcarbamoyl-5-methoxypyrazole | Colorless Prisms | Hydrated Methanol | 88–89 | $C_{13}H_{14}O_2N_3Br$ (324.2) | 48.17 (48.10 | 4.35 4.31 | 12.96 12.91) |
| 73 | 1-(p-methoxyphenyl)-3-N,N-dimethylcarbamoyl-5-methoxypyrazole | Colorless Prisms | Ethanol-Petroleum ether | 112–113.5 | $C_{14}H_{17}O_3N_3$ (275.3) | 61.08 (60.95 | 6.22 6.18 | 15.26 15.18) |
| 74 | 1-(p-methoxyphenyl)-3-morpholinocarbonyl-5-methoxypyrazole | Colorless Needles | Ethyl ether-Petroleum ether | 86–87 | $C_{16}H_{19}O_4N_3$ (317.3) | 60.56 (60.59 | 6.03 5.92 | 13.24 13.10) |

While the invention is described in detail with reference to specific embodiments thereof, it is to be noted that various changes and modifications can be made therein without departing from the spirit and the scope of the invention.

What is claimed is:

1. Pyrazole compounds represented by the formula

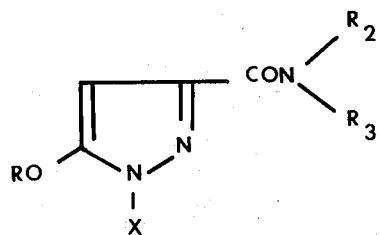

wherein R represents an alkyl group of 1 to 4 carbon atoms, X represents a mono- or di-substituted phenyl group wherein the substituents may be the same or different and each represents an alkyl group of 1 to 4 carbon atoms, an alkoxy group of 1 to 4 carbon atoms, a trifluoromethyl group, a nitro group, an amino group or a halogen atom; or a substituted or unsubstituted benzyl group wherein the substituent is a halogen atom, $R_2$ represents a hydrogen atom or an alkyl group of 1 to 4 carbon atoms and $R_3$ represents a hydrogen atom, a hydroxyalkyl group of 1 to 4 carbon atoms, an alkyl group of 1 to 4 carbon atoms or a substituted aminoalkyl group of 1 to 4 carbon atoms.

2. 1-(p-Tolyl)-3-N,N-dimethylcarbamoyl-5-methoxypyrazole according to claim 1.

3. 1-(m-Trifluoromethylphenyl)-3-N,N-dimethylcarbamoyl-5-n-butoxypyrazole according to claim 1.

4. 1-(m-Chlorophenyl)-3-N,N-dimethylcarbamoyl-5-methoxypyrazole according to claim 1.

5. 1-(m-Chlorophenyl)-3-carbamoyl-5-methoxypyrazole according to claim 1.

6. 1-(p-Chlorobenzyl)-3-N-methylcarbamoyl-5-methoxypyrazole according to claim 1.

7. 1-(m-Chlorophenyl)-3-N-methylcarbamoyl-5-methoxypyrazole according to claim 1.

8. 1-(m-Chlorophenyl)-3-N-ethylcarbamoyl-5-methoxypyrazole according to claim 1.

9. 1-(m-Bromophenyl)-3-N-methylcarbamoyl-5-methoxypyrazole according to claim 1.

10. 1-(m-Bromophenyl)-3-N-ethylcarbamoyl-5-methoxypyrazole according to claim 1.

11. 1-(m-Bromophenyl)-3-N,N-dimethylcarbamoyl-5-methoxypyrazole according to claim 1.

12. Pyrazole compounds represented by the formula

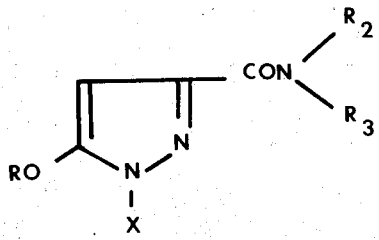

wherein R represents a straight or branched chain alkyl group having 1 to 4 carbon atoms, $R_2$ represents a hydrogen atom or a methyl group, $R_3$ represents a methyl group, and X represents a m- or p-monosubstituted phenyl group wherein the substitutent in a chlorine atom, a bromine atom or a trifluoromethyl group, or X represents a p-monosubstituted benzyl group wherein the substitutent is a chlorine atom or a bromine atom.

13. A compound of claim 12, wherein R is a methyl group and X is a m-chlorophenyl group or a m-bromophenyl group.

14. A compound of claim 12, wherein X is a m-chlorophenyl group.

* * * * *

UNITED STATES PATENT AND TRADEMARK OFFICE
CERTIFICATE OF CORRECTION

PATENT NO. : 3,953,467
DATED : April 27, 1976
INVENTOR(S) : Hajime FUJIMURA et al It is certified that error appears in the above-identified patent and that said Letters Patent are hereby corrected as shown below:

Correct Item [54] on face of patent to read as follows:

PYRAZOLE DERIVATIVES AND PROCESS
FOR PREPARING THE SAME

Correct Item [75] on face of patent to read as follows:

Hajime Fujimura, Kyoto;
Mikio Hori and Osamu Ootani, Gifu;
Sachio Ohno, Tadashi Kitamikado,
Kiyoshi Kato and Mitsuaki Nagasaka,
of Aichi, all of Japan.

Signed and Sealed this

Thirty-first Day of August 1976

[SEAL]

Attest:

RUTH C. MASON
*Attesting Officer*

C. MARSHALL DANN
*Commissioner of Patents and Trademarks*